United States Patent
Verma et al.

(10) Patent No.: US 11,532,384 B2
(45) Date of Patent: Dec. 20, 2022

(54) PERSONALIZED OFFLINE RETRIEVAL OF DATA

(71) Applicant: International Business Machines Corporation, Armonk, NY (US)

(72) Inventors: Archit Verma, New York, NY (US); Jennifer A. Mallette, Vienna, VA (US); Ruchi Asthana, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 341 days.

(21) Appl. No.: 16/838,909

(22) Filed: Apr. 2, 2020

(65) Prior Publication Data

US 2021/0313017 A1    Oct. 7, 2021

(51) Int. Cl.
*G16H 10/20*    (2018.01)
*G16H 10/65*    (2018.01)
(Continued)

(52) U.S. Cl.
CPC ............ *G16H 10/20* (2018.01); *G06F 16/22* (2019.01); *G06F 16/2372* (2019.01);
(Continued)

(58) Field of Classification Search
CPC .. G16H 10/20; G16H 10/65; G06F 16/24573; G06F 16/22; G06F 16/2458; G06F 16/2372; G06F 16/24575
(Continued)

(56) References Cited

U.S. PATENT DOCUMENTS

| 9,760,681 B2 * | 9/2017 | Douglass ............... G16H 10/60 |
| 9,782,075 B2 | 10/2017 | Redei |

(Continued)

FOREIGN PATENT DOCUMENTS

| JP | 2012053922 A | 3/2012 |
| KR | 101818022 B1 | 1/2018 |

OTHER PUBLICATIONS

Mckeown et al., Generating Patient-Specific Summaries of Online Literature, 1998, 34-43, AAAI Technical Report SS-98-06, AAAI (www.aaai.org).

(Continued)

*Primary Examiner* — Giovanna B Colan
(74) *Attorney, Agent, or Firm* — Levine's Tech Consulting, LLC; Frank E. Levine

(57) ABSTRACT

An approach is disclosed for storing information tailored to a user and a condition to be accessed offline to fit on a local device. The information is retrieved from a set of online sources by a device. The retrieved information is tailored according to a criteria and the condition to form a curated data. An index is provided to access the curated data. The index is used to answer queries. Responsive to identifying a question without an answer found in the curated data when the device is off-line, searching for the answer when the device is online. Responsive to finding the answer online, pruning the curated data by eliminating lower importance data as needed to store higher importance data based on an availability of space allocated to store the curated data on the local storage device, and updating the curated data stored on the local device.

20 Claims, 10 Drawing Sheets

(51) Int. Cl.
    *G06F 16/23*         (2019.01)
    *G06F 16/2458*    (2019.01)
    *G06F 16/2457*    (2019.01)
    *G06F 16/22*         (2019.01)

(52) U.S. Cl.
    CPC .... *G06F 16/2458* (2019.01); *G06F 16/24573* (2019.01); *G06F 16/24575* (2019.01); *G16H 10/65* (2018.01)

(58) Field of Classification Search
    USPC ........................................ 705/3; 707/600–899
    See application file for complete search history.

(56) References Cited

U.S. PATENT DOCUMENTS

| | | | | |
|---|---|---|---|---|
| 10,997,663 | B1* | 5/2021 | Wyatt | G06Q 40/08 |
| 2006/0074883 | A1* | 4/2006 | Teevan | G06F 16/9535 |
| 2009/0177644 | A1* | 7/2009 | Martinez | G06Q 30/0201 |
| | | | | 707/999.005 |
| 2010/0306773 | A1* | 12/2010 | Lee | G06F 9/5077 |
| | | | | 718/1 |
| 2011/0125744 | A1* | 5/2011 | Immonen | G06F 16/29 |
| | | | | 707/769 |
| 2014/0324776 | A1* | 10/2014 | Novak | G06F 16/178 |
| | | | | 707/827 |
| 2015/0066538 | A1* | 3/2015 | Dantsker | G16H 40/63 |
| | | | | 705/2 |
| 2015/0186415 | A1* | 7/2015 | Li | H04W 4/029 |
| | | | | 707/755 |
| 2015/0261800 | A1* | 9/2015 | Botero | G06F 16/22 |
| | | | | 707/610 |
| 2017/0004323 | A1* | 1/2017 | Balachandran | G06F 21/6209 |
| 2017/0076046 | A1* | 3/2017 | Barnes | G06F 40/40 |
| 2017/0237606 | A1 | 8/2017 | Canessa et al. | |
| 2018/0020918 | A1 | 1/2018 | Redei | |
| 2018/0146354 | A1* | 5/2018 | Patel | H04W 4/90 |
| 2018/0239948 | A1* | 8/2018 | Rutschman | G06V 10/40 |

OTHER PUBLICATIONS

Teufel et al., Personalizing Retrieval of Journal Articles for Patient Care, Proc AMIA Symp., 2001, 696-700, AMIA, Inc.

* cited by examiner

800

Condition Specific Metadata
800

Owner, Contact info, (e.g. email)
810

Access rights (granularity for access to the data per user, group, or process)
820

Condition details (e.g.Type 1 diabetes (T1D) )Most people with T1D spend the majority of their time with blood-glucose levels outside the recommended healthy range, which can lead to potentially deadly episodes of hyperglycemia (high blood sugar) and hypoglycemia (low blood sugar).
830

Current treatment detail (e.g., Insulin Metformin, diet, exercise,.Pramlintide (Symlin)
840

Alternative treatment options (e.g.Monitoring blood sugar can be done using traditional blood-sugar meters or continuous glucose monitors (CGMs). Measuring the amount of carbohydrates and factoring the insulin to carb (I:C) ratio helps maintain stable blood-sugar levels after eating.
840

Container with relevant files
860

Priority mapping
870

Personally identifiable information (PII) discovery and mapping details
880

*FIG. 8*

PERSONALIZED OFFLINE RETRIEVAL OF DATA

BACKGROUND

The present invention relates to a computing environment, and more particularly to a computer program, method, and system for collecting data accessible offline to answer questions tailored to a user and a condition.

SUMMARY

According to one embodiment of the invention, there is a method that includes a processor and a local storage device accessible by the processor for storing information tailored to a user and a condition. The information is retrieved from a set of online sources by a device. The retrieved information is tailored according to a criteria and the condition to form a curated data. The curated data is stored on the local storage device. An index is provided to access the curated data. The index is used to answer received questions. Responsive to identifying a question without an answer found in the curated data when the device is off-line, searching for the answer when the device is online. Responsive to finding the answer online, pruning the curated data by eliminating lower importance data as needed to store higher importance data based on an availability of space allocated to store the curated data on the local storage device, and updating the curated data stored on the local device.

According to one embodiment of the invention, there is provided an information handling system including at least one processor and a local storage device accessible by the processor executing instructions implementing steps of the method that provides for storing information tailored to a user and a condition.

According to one embodiment of the invention, there is provided a computing program product executing instructions on at least one processor including a local storage device accessible by the processor having the steps of the method that provides for storing information tailored to a user and a condition.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention will be apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings, wherein:

FIG. 8 shows a table of an example of condition specific metadata;

DETAILED DESCRIPTION

Figure 1:
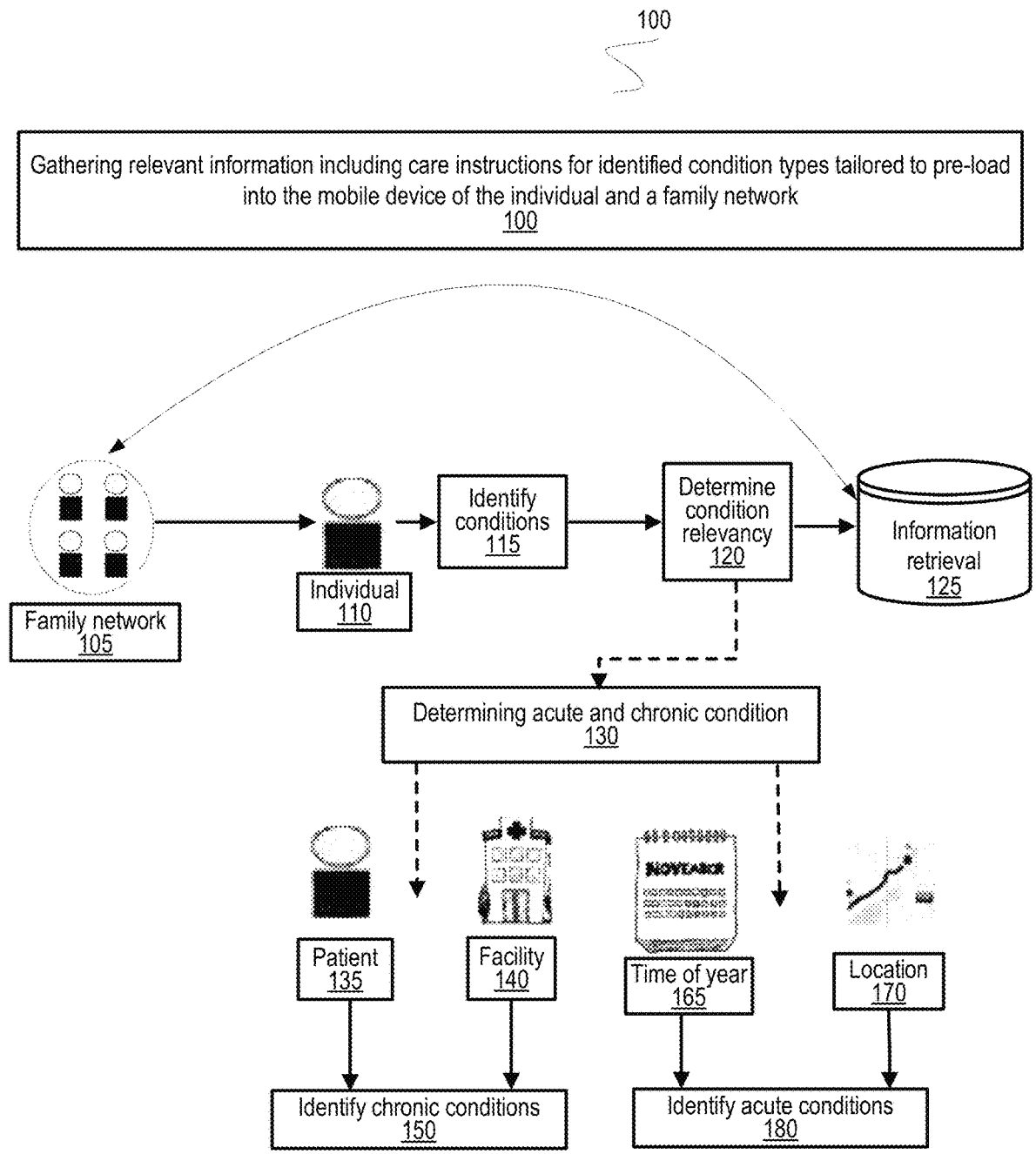
FIG. 1 shows a diagram depicting a schematic overview of a system having support for gathering, tailoring, and storing information relevant to a user and a condition for offline usage.

Over 150 natural disasters occur each year in the US, during which many are unable to find treatment information for relevant acute and chronic conditions when they happen. Today there is a lack of an offline tool that provides people relevant information regarding treatment options for conditions they or a family member maybe susceptible to a natural disaster.

In a hypothetical scenario, Alice, Bob, and Eve are living in a town where a hurricane is predicted to hit. They may be able to prepare for some common problems such as, lack of food, unsafe shelter, lack of clean water source, and lack of electricity. However, preparation for some of these conditions may be difficult due to various circumstance. For example, obtaining a clean safe shelter may not be practical. However, given some available tools, information about how to build a temporary shelter using the available tools might be helpful under some emergency circumstances. In addition, they would not typically be prepared for when Alice cuts her foot stepping on shattered window glass or Bob (an asthma prone neighbor) encounters a hurricane trigger. If Eve has access to the internet, she could find solutions for helping Alice and Bob, but during a natural disaster this is not a dependable approach. Given the deficiencies of the prior art, there is a clear benefit to preloading information to aid individuals during a natural disaster or other emergency condition when internet access is not available or limited.

With embodiments disclosed herein, information may be preloaded for situations that may be faced by someone tailored to their personal situation and concerns. Concerns may include, but are not limited to existing, reported, or searched for conditions. These conditions may pertain to existing or likely acute and chronic conditions the user or someone in that user's family network has exhibited an interest in retrieving information. These conditions and remediation strategies can be based off factors such as personal history, the location, and time of the year. The information gathered may be tailored to optimize assistance during an offline emergency. The offline information may, for example, include emergency health care and treatment. The treatment for a patient may be given by the patient or a caregiver.

In an online setting, information about the user (e.g. patient history, location, and time of year) may be collected to determine the conditions, such as, but not limited to chronic and acute conditions that affect the user during the current time period. Based off the details of the condition, relevant information, such as care instructions or alternative resource by-pass relevant to the conditions identified may be pre-loaded on the user's device. The user's device may be, for example, a portable or mobile device, hereafter referred to as mobile. The retrieved information may also be pre-loaded on the mobile devices of other users in the family network in the case of a potential emergency when users are offline. The diagrams disclosed herein include schematic processes and steps depicting example embodiments of the invention disclosed herein.

There are many situations when people need to access information useful in an emergency, such as, health care information, but do not have internet access. Applications today can provide this guidance but tend to require remote data access or an internet connection in order to access some larger database and return the proper answers. As a solution, embodiments disclosed herein may be tailored to an individual's emergency needs, such as, but not limited to, an individual's medical needs in offline situations (e.g. natural disasters, third world countries, power outages). In these circumstances, the individual may use a device with less storage (i.e. mobile). In this case, downloading an entire database is infeasible. In an embodiment, personal profiles are used to curate data, such as, medical, to fit on an offline device. In an embodiment, for a user, the user's features and past medical conditions are used to curate the data that is relevant. With this smaller subset of the data and a smaller search index, the necessary storage size is decreased so that the application can be accessed offline. This assumption of low storage is crucial in the medical field as various online sources have excessively large datasets, preventing them from being accessed from a phone without a high-speed internet connection.

FIG. 1 depicts an embodiment of the invention herein depicting a schematic flow of steps taken by a process 100 for gathering relevant information including care instructions for identified condition types tailored to be pre-loaded into the mobile device of the individual 110 and on a family network 105. The search request may search various online sources and perform information retrieval 125. At step 115, the process identifies conditions. The conditions may be gathered from applying natural language processing (NLP) to search requests from the individual 110 or from search requests from the family network 105. The conditions may be determined based on profile information or other means. At step 120, the process determines condition relevancy. At step 130, the process may for example, determine acute and chronic conditions. At step 150, the process identifies chronic conditions. At step 180, the process identifies acute conditions. Consider a family network 105 of individuals, where each member may have a mobile device. In an online setting, information about the patient 135, for example, patent history retrieved from a facility 140, location 170, and time of year 165 may be collected to identify the chronic conditions 150 and to identify the acute conditions 180 that affect the user during the current time period. Based off the details collected while online, the collected information, including instructions relevant to the conditions, may be stored on the user's mobile device along with the mobile devices of other users in the family network. Prior to storing, a remote staging area may be used, such as, a database server and prioritized. Once stored on the user's mobile device the information may be retrieved in the case of an emergency when the users are offline. Patient 135 may self-report on conditions they find relevant to themselves as input to identify chronic conditions 150. Similarly, facility 140 reports, such as, for example, but not limited to hospital, images, therapies, and laboratory reports, may be stored as electronic medical records (EMRs) or electronic health record (EHR) which are a digital version of the paper charts in the clinician's office. They may contain the medical records including treatments that are digital version of the paper charts in the clinician's office. These records may be retrieved while online and may be used as input to identify chronic conditions 150 and be used as input to identify acute conditions 180. An EMR may contain both the medical details and treatment.

Longitudinal data, sometimes called panel data, is a collection of repeated observations of the same subjects, taken from a larger population, over some time—and is useful for measuring change. Facility 140 system reporting may include longitude data (e.g. EMR, EHR) reporting based on location 170 and time of year 165 for the location 170. That is, the information may include location 170 specific information for the time of year 165 and may contain information about upcoming weather conditions and potential natural disasters (e.g. thunderstorms, flashfloods, earthquakes, tornadoes, mudslides, sink holes, wildfires, etc.). Similar information may be obtained via other means. Once a concern for a potential natural disaster is identified, information related to a predicted condition may be retrieved while online. The steps may be tailored to a successful or recommended process which may include details based on a history of successful techniques and practices for previous similar conditions in the area. Also, steps to avoid may also be obtained to include problems or failed processes having undesirable outcomes when previously used. While making preparation for some conditions, some typical recommended preparations may turn out to be difficult, not realistic, or very expensive. When recommended preparations are not likely to be followed, other alternative after-the-fact or more feasible to follow steps during the actual emergency may be retrieved. In some embodiments, the alternative steps may be retrieved while the device is online and tailored to be stored on the local device.

Figure 2:
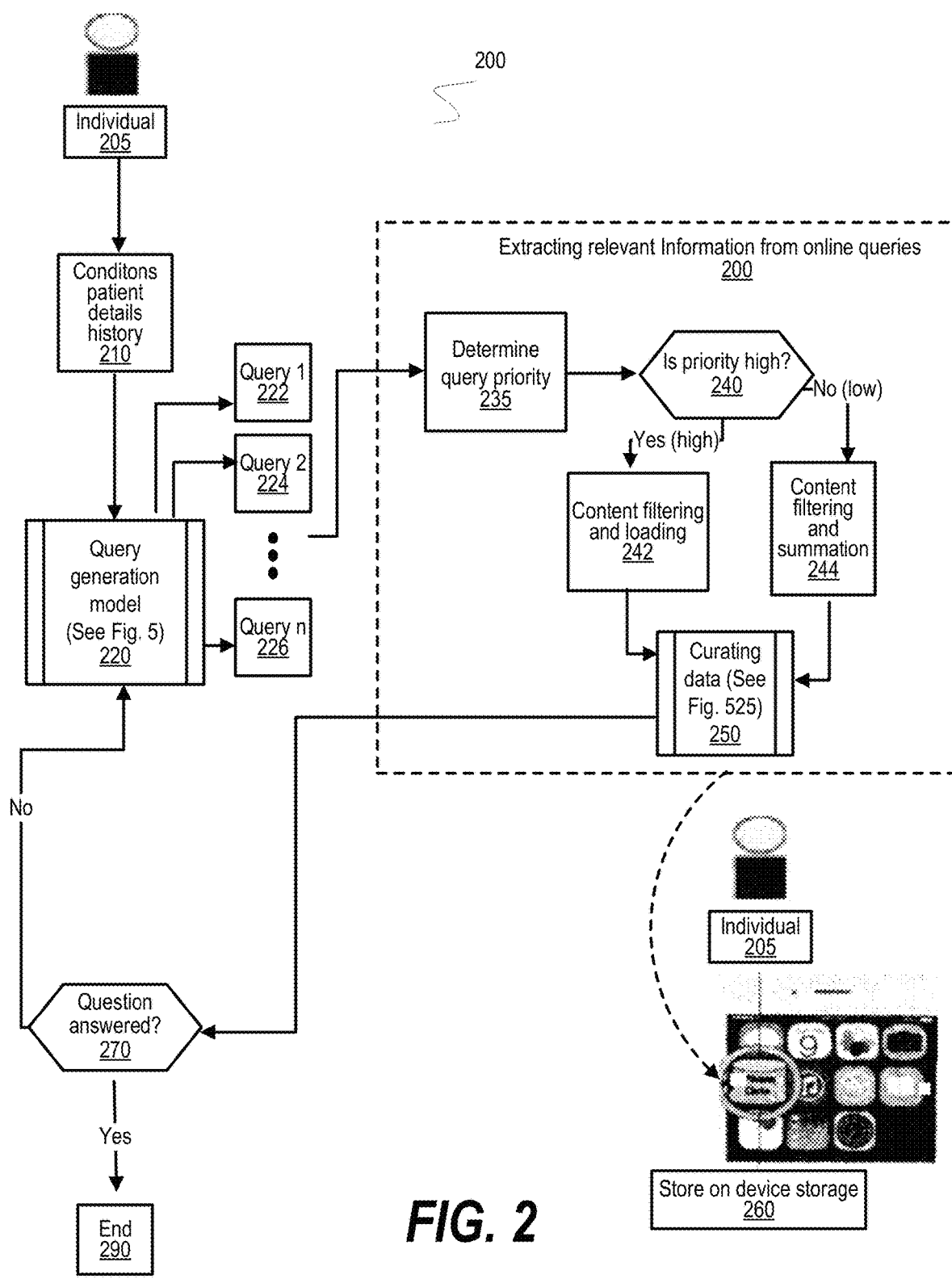
FIG. 2 shows a schematic view of extracting relevant information from online queries.

FIG. 2 processing commences at 200 and shows the steps taken by a process for extracting relevant Information from online queries. At step 235, the process determines query priority. The process determines as to whether is priority high (decision 240). If is priority high, then decision 240 branches to the 'yes (high)' branch. If not is priority high, then decision 240 branches to the 'no (low)' branch. At step 242, the process performs content filtering and loading. The content filtering is prioritized to enable capturing more information compared to step 244 where the process performs the process contents filtering and summation when the priority is low. At step 250, the process curate's data by executing the relevant content orchestrator 525 (see FIG. 525 and corresponding text for curating data processing details). The curated data may be stored on the device storage 260 on behalf of the individual 205. The device storage 260 could be, for example, a hard drive, a CD-ROM, a DVD-ROM, a flash media, a "thumb" drive, a memory stick, and the like. The device itself could be a, for example, but not limited to a phone, a laptop, and the like.

The curation step 250 considers an importance of the information, the available disk space, and a history of answering either the same question or similar questions by proceeding to step 270. Repeated similar questions may indicated a problem with the retrieved results and could promote a low priority question to a high priority question. The process determines as to whether question is answered (decision 270). If question is answered, then decision 270 branches to the 'yes' branch to step 290, where the process ends. If question is not answered, then decision 270 branches to the 'no' branch to determine questions to query by proceeding to utilize the predefined process 220 that performs the query generation model routine (see FIG. 5 and corresponding text for processing details). The query generation model 220 utilizes information from or about the individual 205 including condition information, such as, patient details and history 210. The query generation model 220 may generate multiple queries, e.g., query 1 222, query 2 224, . . . , query n 226. These queries may be derived from previous user queries. They may be derived from analysis of tracked conditions, or other approaches utilizing a machine learning approach.

Figure 3:
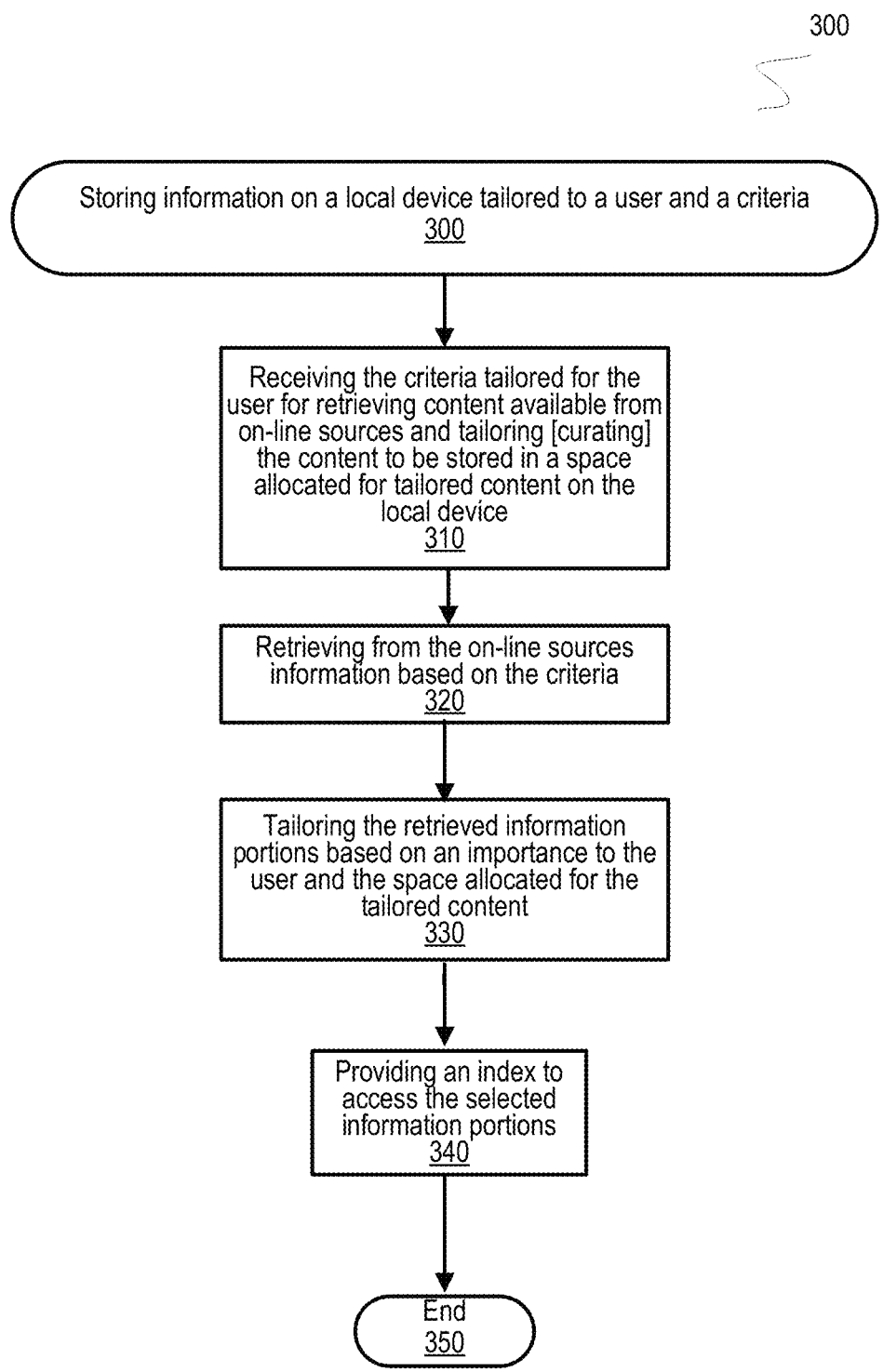
FIG. 3 shows a flowchart depicting steps taken for storing information on a local device tailored to a user and a criteria.

FIG. 3 processing commences at 300 and shows the steps taken by a process that stores information on a local device tailored to a user and a criteria. At step 310, the process receives the criteria tailored for the user used for retrieving content available from online sources and tailoring [curating] the content to be stored in a space allocated for the tailored content on the local device. The criteria may be identified by various means, for example, but not limited to user queries, from condition information based on a user profile, from medical records, and from location and time of year including current weather conditions. At step 320, the process retrieves from the online sources information based on the criteria. The sources may require permission where the user needs to login. The user may decide to schedule the gathering of the information. Once the conditions for gathering the information are met, the user may, for example, be prompted to login to medical records tailored to the user. In some embodiments, this support may be supplied by a graphical user interface allowing for detailed selections that identify conditions under which attempts to access the information may be attempted. At step 330, the process tailors the retrieved information portions based on an importance to the user and the space allocated for the tailored content. The determination of space may be determined initially by determining available space and setting allocation bounds. In an embodiment, the allocation bounds may be included in condition specific metadata that is modifiable by the user. At step 340, the process provides an index to access the selected information portions. FIG. 3 processing thereafter ends at 350. While online, a staging area may be used to collect and prepare the information to be copied to a storage device on the mobile device. In some embodiments, a knowledge graph (KG) may be constructed to have a hierarchical representation of the collected information. The KG may have connected nodes formed from accessing a knowledge base for a domain or derived from an online index found in the online source. The local index constructed for usage on the local device could have a self-balancing tree data structure, such as, a B-Tree or other technology, such as, but not limited to hash tables. In some embodiments, detection of an unable to write due to no free space available may be detected. Under that condition or under user direction the on-line data may be pruned to allow higher priority information to be stored locally by removing or trimming lower priority information.

Figure 4:
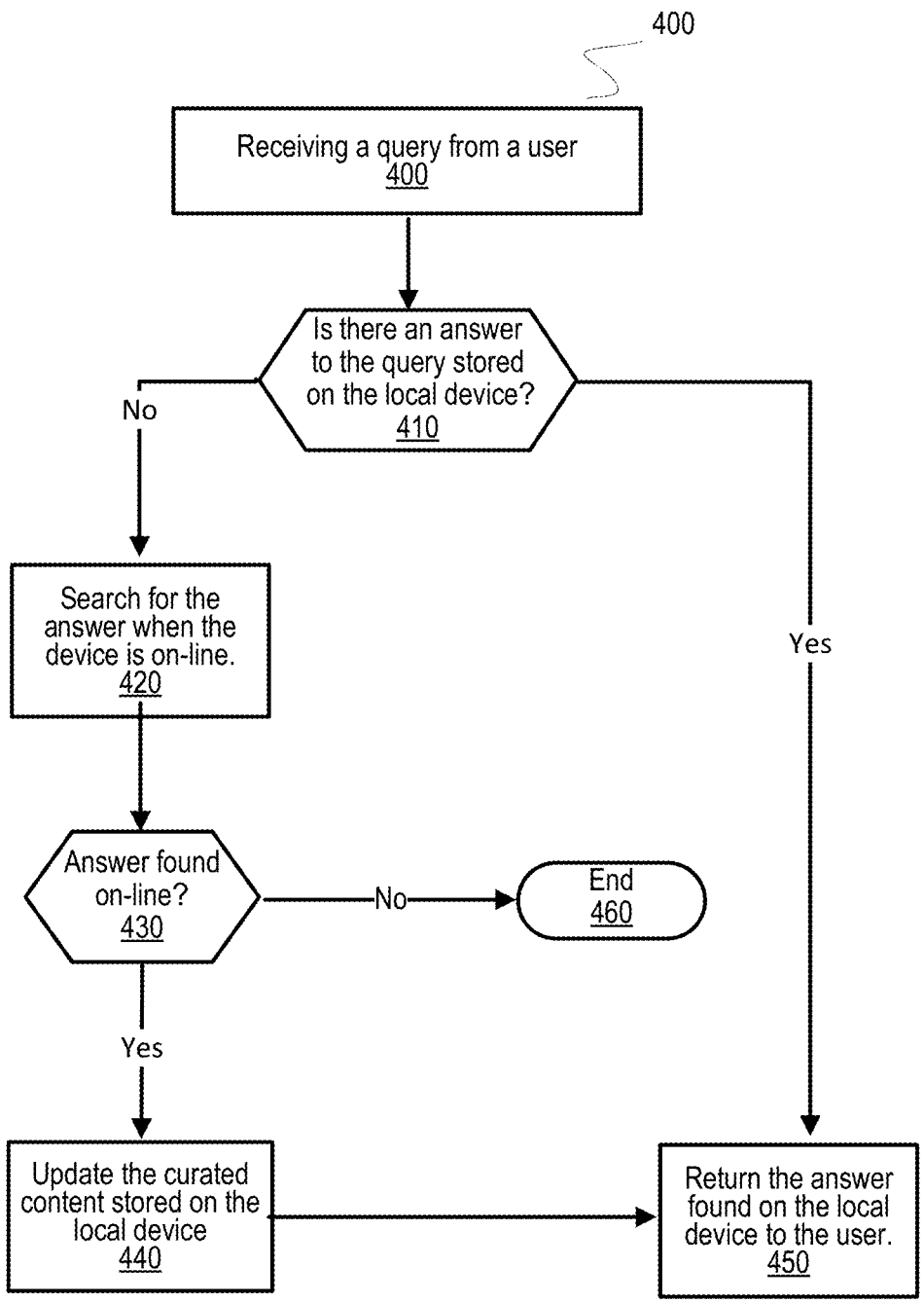
FIG. 4 shows a flowchart depicting steps taken for processing a query received from a user.

FIG. 4 processing commences at 400 and shows the steps taken by a process that receives a query from a user. The process determines as to whether is there an answer to the query stored on the local device (decision 410). If is there an answer to the query stored on the local device, then decision 410 branches to the 'yes' branch. On the other hand, if not is there an answer to the query stored on the local device, then decision 410 branches to the 'no' branch. At step 420, the process searches for the answer when the device is online. The process determines as to whether answer found online (decision 430). If answer is found online, then decision 430 branches to the 'yes' branch. On the other hand, if not is answer found online, then decision 430 branches to the 'no' branch. At step 440, the process updates the curated content stored on the local device. At step 450, the process returns the answer found on the local device to the user. FIG. 4 processing thereafter ends at 460. In an embodiment, the patient information may be stored in the form of a knowledge graph where different symptoms and treatments are edges in the graph. This graph can be adjusted based on information related to location, time of year and environmental factors. For instance, if electricity is needed for the preferred treatment approach for a condition, but the approaching natural disaster is likely to cause power cuts, users might need alternate electricity independent strategies on how to treat the condition loaded onto their mobile device. A person's chronic conditions may be based off personal reporting, electronic health records, and longitudinal health data. A person's acute condition may be based off where they live and what time of the year it is. Weather interface API's may be used to determine natural disasters or severe weather conditions based off the location and time of year. The most relevant conditions may be determined by sorting through the identified acute and chronic conditions. Querying relevant conditions against data sources that contain information about acute and chronic conditions as well as step-by-step guides for treatment and care. The mobile device of the person and others in the care network may be pre-populate with information and care instructions for the identified relevant conditions.

Figure 5:
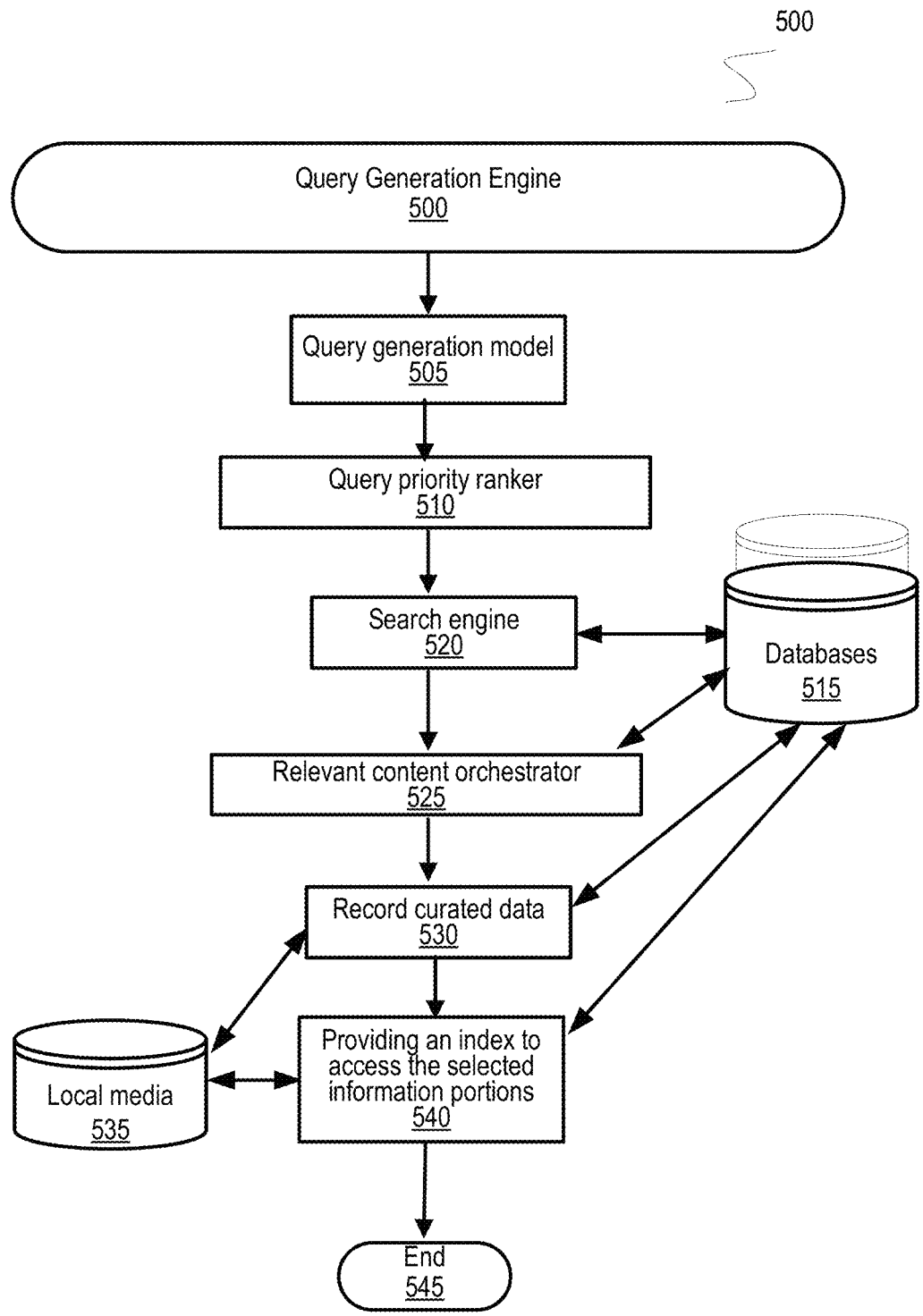
FIG. 5 shows a flowchart depicting steps taken by a query generation engine.

FIG. 5 processing commences at 500 and shows the steps taken by a query generation engine. In an embodiment, the query generation engine runs a query generation model 505 which generates a set of search queries. The query generation model 505 may construct queries based on identified conditions 115. These search queries may then be passed into a query priority ranker 510, which ranks queries based on their relevance to the user such as at step 120. Thresholds may be set for assigning queries with a ranked class, for example, a high priority class, a medium priority class, or low priority class. The queries may then be input to a search engine 520 that gathers and store relevant information using, for example, a relevant content orchestrator 525. For high priority queries, the relevant content orchestrator 525 may search large medical databases 515 for articles with relevant information. It collects articles with the most relevant information and stores those in a curated database. For medium priority queries, the relevant content orchestrator 525 may be searching for alternative tooling that might be used for constructing a shelter when power is not available. For low priority queries, the relevant content orchestrator 525 may also search large medical databases 515 for articles, collect articles with the most relevant information to an individual, summarize relevant content, and store (only the relevant) data on a curated database. Relevancy for the relevant content orchestrator 525 may be influenced by the following: (1) Data the user's mobile device can handle. (2) How at risk the user is. (3) Confidence and relevance of queried conditions. (4) How much memory the user wants to allocate for this application. (5) Download data from the curated database that is specified to be loaded onto the local media 535 for the mobile application (for access in offline situations). (6) At step 540, the process provides an index to access the selected information portions of the downloaded data. FIG. 5 processing thereafter ends at 545.

Figure 6:
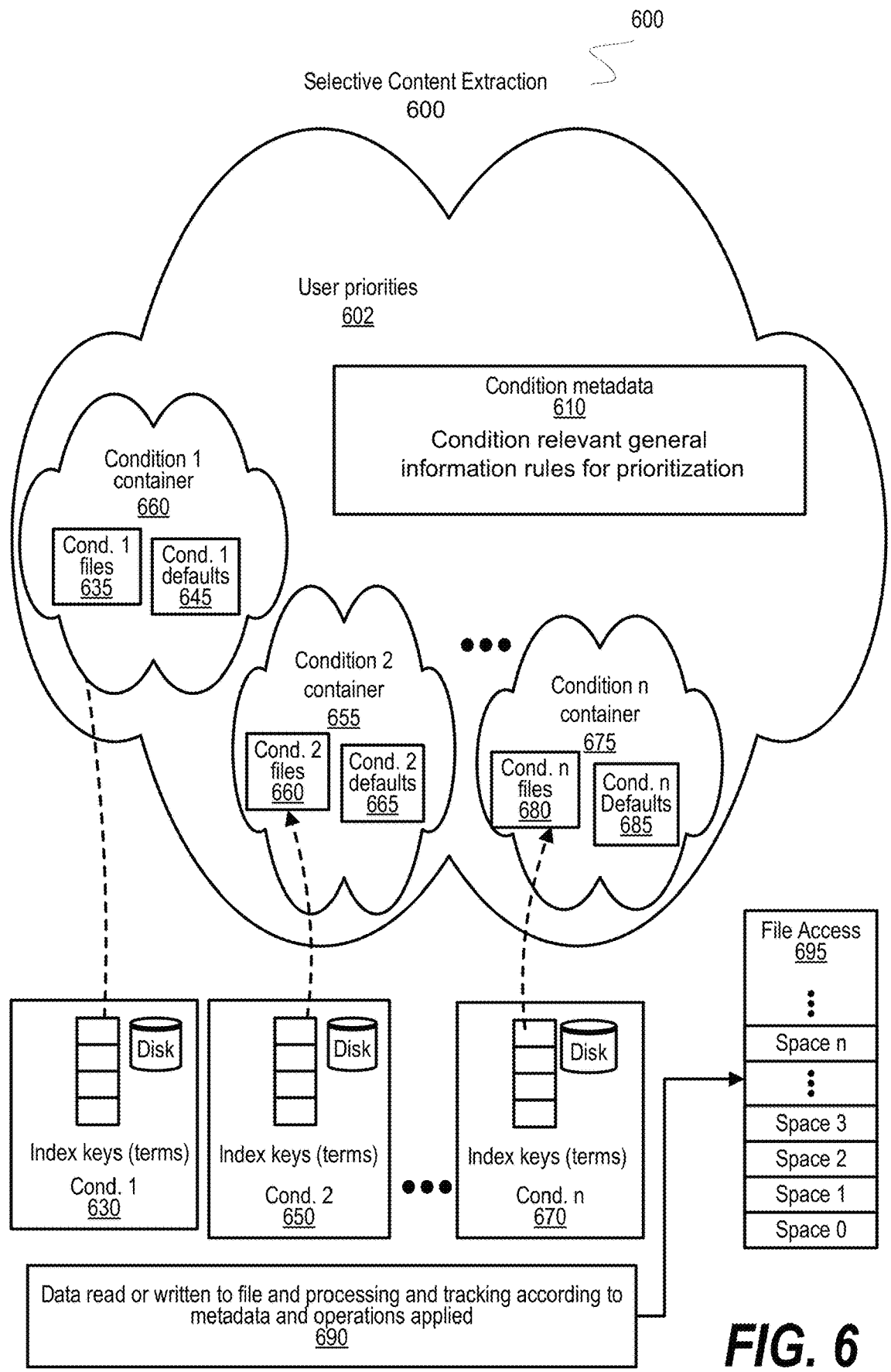
FIG. 6 shows a schematic view depicting selective content extraction.

FIG. 6 depicts a schematic view of an embodiment showing information that may be used for selective content extraction 600. The user's priorities 602 may include condition metadata 610 which may include condition relevant general information rules for prioritization. Each condition may have its own container, with separated files and default rules. A container may be, for example, a folder or a directory. For example, condition 1 files container 635 includes condition 1 files 640, condition 1 default rules 645, condition 1 index keys or terms 630. Condition 2 files container 655 includes condition 2 files 650, condition 2 default rules 665, and condition 2 index keys or terms 650 . . . Condition n files container 675 includes condition n files 680, condition n default rules 685, and condition n index keys or terms 670. The process reads or writes data to file via a file access 695 and processes and tracks according to metadata and operations applied 690. In an example embodiment, the Space 1, Space 2, . . . Space n entries may become pointers to containers or index entries for identified conditions, such as, condition 1 index keys or terms 630, condition 2 index keys or terms 650, . . . , condition n index keys or terms 670.

Figure 7:
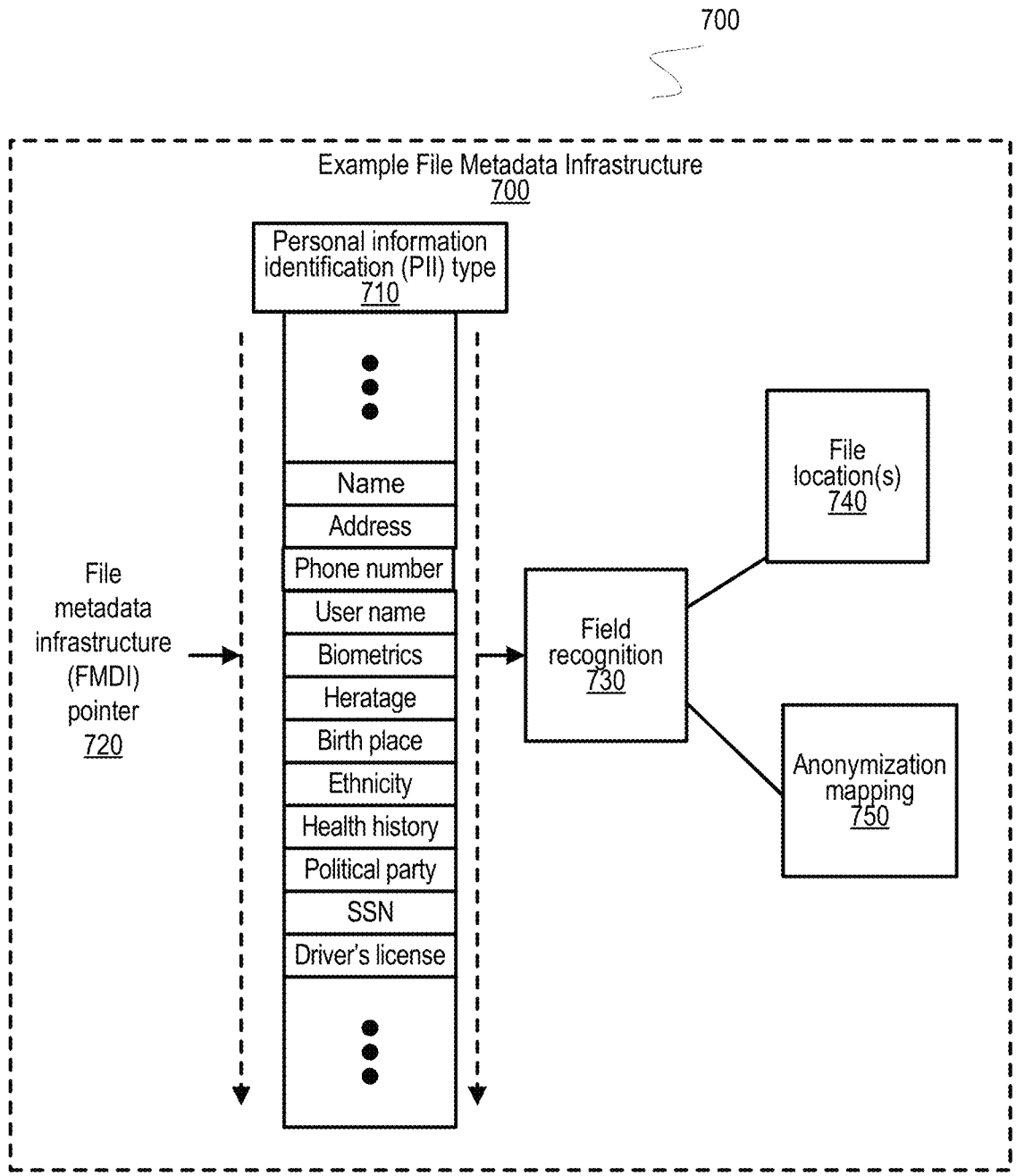
FIG. 7 shows a schematic view depicting an example of a file metadata infrastructure.

FIG. 7 depicts a schematic view of an example file metadata infrastructure 700. A file metadata infrastructure (FMDI) pointer 720 points to a structure that identifies a personal information identification (PII) type 710 utilizing a field recognition 730 with file location(s) 740. In an example embodiment, field type may be defined by mapping numbers to type or by self-defining character strings. An interface may be used to perform field recognition 730 which returns file location(s) 740 and may also allow for anonymization mapping 750 depending upon security needs. In an embodiment, users or their doctors may enter the user's personal data. Examples of personal data may include a personal profile identifying name, address, phone number, user name (for an account), biometrics details, heritage, birth place, race, ethnicity, health history, political party, social security number (SSN), driver's license number, age, height, weight, and the like. The personal profile may include a disease profile, for example, obesity, cancer, diabetes, and the like. The personal profile may include a geographical profile indicating where they work and currently live [e.g., born in Thailand, lives in NYC]. In an embodiment, based on the various personal profiles, many different types of categories may be supported, such as, but not limited to, not sensitive, sensitive personal based on discovery, mild sensitive personal, medium sensitive personal, highly sensitive personal, business sensitive, business confidential, and the like. There are many ways that the information may be classified and/or identified. In some embodiments the fields may be known based on a template in a form, a user classification, a scan using regular expression, etc. Having personal information available in one or more files related to a single person may change or affect the sensitivity of the information in the files. For example, being able to identify the specific person for which the information refers may be considered highly sensitive depending on how the data is used. Information in the metadata identifies how user data may be used and tracks copies of user data.

Various approaches may be used to create, revise, update, and delete (CRUD) metadata structures with metadata entries (MDEs) used to implement the concepts disclosed herein. The implementation would depend on details of the support needed and the base operating system. Although various approaches may be used, conceptually the metadata structures may be considered a link list of structures where individual metadata entries (MDEs) may be added, removed, and updated by allocating and freeing memory areas to hold the structures. In some embodiments, a doubly linked list may be used. In other embodiments entries may be identified by unique ids and be found by using hash tables supporting collisions. The unique ids could be considered a key and may be constructed by various system unique elements, such as, by combining container name or container id with a file name and an i-container id. Since the system requirements may vary considerably, some example embodiments are described herein to cover some different ranges of environments. Many of the concepts described herein could be implemented on a single system with a single hard file being subject to a single unrecoverable failure. Other environments could support high availability with, for example, Redundant Array of Independent Disks (RAID) and backup containers. Recovery could be supported by using write-ahead logging (WAL) protocol. Variations of WAL could be used to ensure consistency for recording auditing information. Content could even be shared between different containers. Other variations, not described, should be understood to be covered by the claims.

FIG. 8 depicts an example of a table with an example of condition specific metadata 800. Entry 810 identifies the process owner's Contact info, (e.g. email). Entry 820 identifies access rights (granularity for access to the data per user, group, or process). Entry 830 identifies conditions details (e.g. Type 1 diabetes (T1D)). Many people with T1D spend much of their time with blood-glucose levels outside the recommended healthy range, which can lead to potentially deadly episodes of hyperglycemia (high blood sugar) and hypoglycemia (low blood sugar). Entry 840 identifies the current treatment detail (e.g. monitoring blood sugar can be done using traditional blood-sugar meters or continuous glucose monitors (CGMs). Entry 850 identifies alternatives treatment options. Measuring the amount of carbohydrates and factoring the insulin to carb (I:C) ratio helps maintain stable blood-sugar levels after eating. Entry 860 identifies containers with relevant files. Entry 870 identifies priorities mapping. Entry 880 identifies personally identifiable information (PII) discovery and mapping details.

Figure 9:
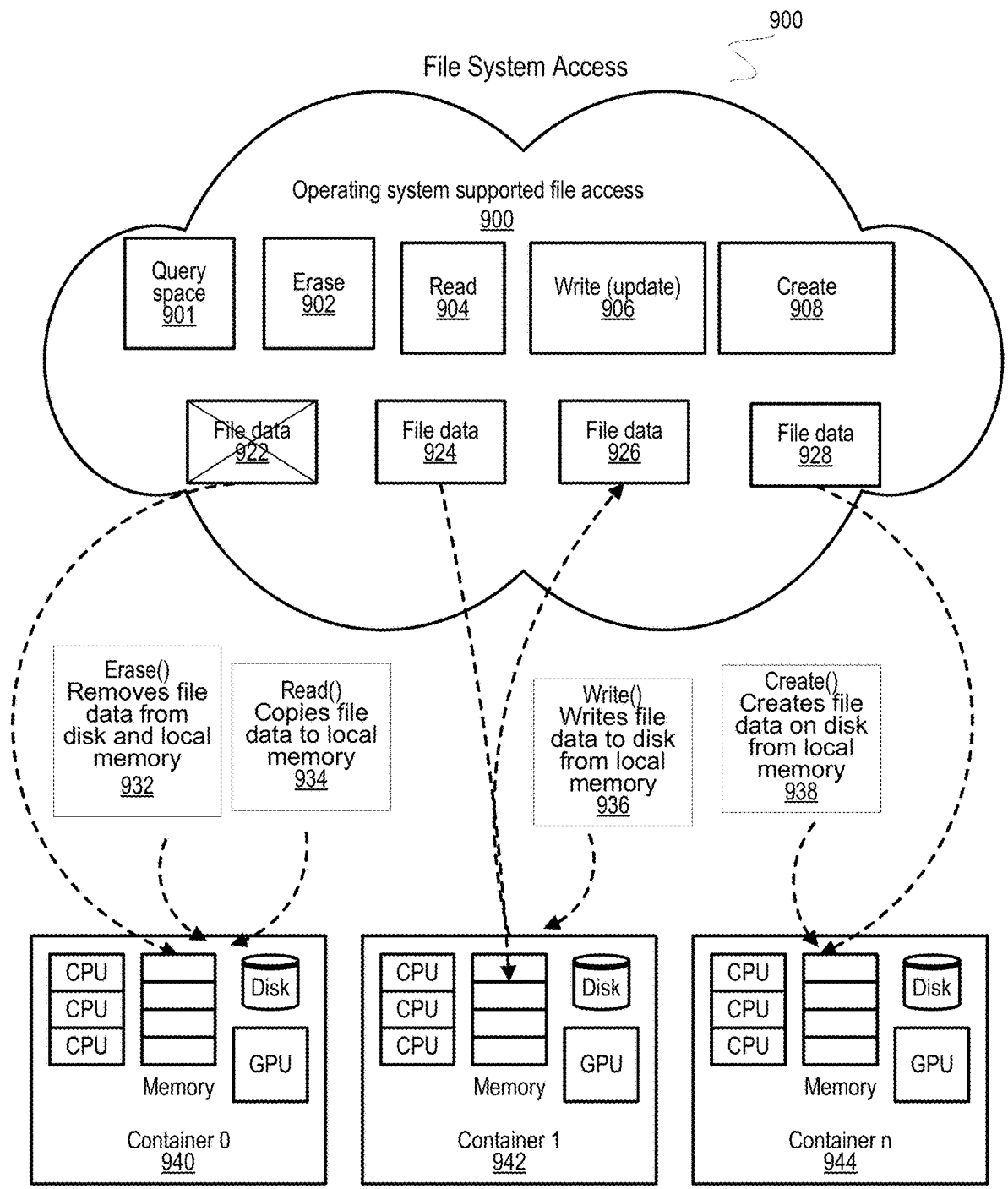
FIG. 9 shows a diagram depicting a schematic overview of an operating system supported file access.

FIG. 9 depicts a schematic view of file system access through the OS where access is through the operating system 900 layer. Basic file operation may include, query space 901, erase 902, read 904, write (update) 906, and create 908. Some of these operations are shown with an indication of a flow of the data (contents) to memory of the files accessed by the file operation. In this schematic view, the erase 902 operation takes place on Container 0 940 where file data 922 is removed from disk and local memory 932. In order to identify all the contents to be erased, the file may need to be decrypted. Decryption may be supported by the file read operations in the hardware or may be a separate step, for example, by a file handler that utilizes the Graphics Processing Unit (GPU) for decryption. The Read 904 operation takes place on Container 1 942 where file data 924 is copied to local memory in Container 1 942. Again, the file may need to be decrypted. Decryption may be supported by the file read operations in the hardware or may be a separate step, for example, supported by a file handler that utilizes the GPU for decryption. The write (update) 936 also takes place on Container 1 942. The updated file data 926 may also be the file data 924 read which may have been updated or may be new data added to the file. In any case, encryption may be required before writing the data to disk from local memory 936. Encryption may be supported by the file write operations in the hardware or may be a separate step supported by a file handler that utilizes the GPU for encryption. The create 938 operation takes place on Container n 944 where file data 928 is in local memory in Container n 944. Again, the file may need to be encrypted. Encryption may be supported by the file write operations in the hardware or may be, for example, a separate step supported by a file handler that utilizes the GPU for encryption. In some embodiments, the usage of space may be controlled by the user. The allocation may be adjustable by a user interface such as a graphical user interface (GUI). In an example embodiment, representations of conditions may be presented with related treatments to use and user selections may be used for viewing more details.

Figure 10:
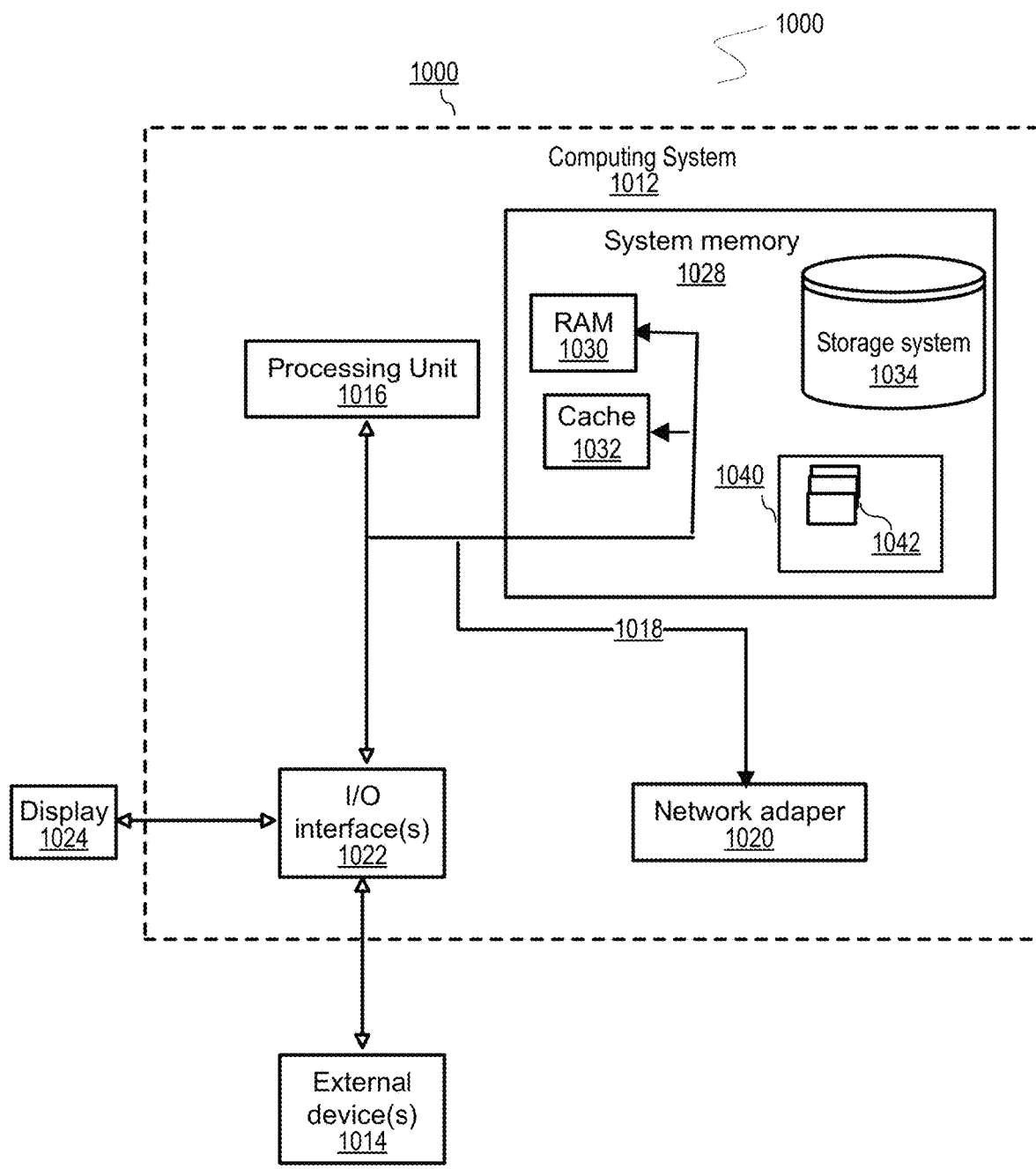
FIG. 10 shows a schematic view of a computing system.

Referring to FIG. 10, a schematic of a processing system 1000 is shown wherein the methods of this invention may be implemented. The processing system 1000 is only one example of a suitable system and is not intended to suggest any limitation as to the scope of use or functionality of embodiments of the invention described herein. Regardless, the system 1000 can implement and/or performing any of the functionality set forth herein. In the system 1000 there is a computer system 1012, which is operational with numerous other general purpose or special purpose computing system environments or configurations. Examples of well-known computing systems, environments, and/or configurations that may be suitable for use with the computer system 1012 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 1012 may be described in the general context of computer system-executable instructions, such as program modules, being executed by a computer system. Generally, program modules may include routines, programs, objects, components, logic, data structures, and so on that perform tasks or implement abstract data types. The computer system 1012 may be practiced in distributed cloud computing environments where tasks are performed by remote processing devices that are linked through a communications network. In a distributed cloud computing environment, program modules may be in both local and remote computer system storage media including memory storage devices.

As shown in FIG. 10, the computer system 1012 in the system environment 1000 is shown in the form of a general-purpose computing device. The components of the computer system 1012 may include, but are not limited to, a set of one or more processors or processing units 1016, a system memory 1028, and a bus 1018 that couples various system components including the system memory 1028 to the processor 1016.

The bus 1018 represents one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA) bus, the Micro Channel Architecture (MCA) bus, the Enhanced ISA (EISA) bus, the Video Electronics Standards Association (VESA) local bus, and the Peripheral Component Interconnects (PCI) bus.

The computer system 1012 typically includes a variety of computer system readable media. Such media may be any available media that is accessible by the computer system 1012, and it includes both volatile and non-volatile media, removable and non-removable media.

The system memory 1028 can include computer system readable media in the form of volatile memory, such as random-access memory (RAM) 1030 and/or a cache memory 1032. The computer system 1012 may further include other removable/non-removable, volatile/non-volatile computer system storage media. By way of example only, a storage system 1034 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 1018 by one or more data media interfaces. As will be further depicted and described below, the system memory 1028 may include at least one program product having a set (e.g., at least one) of program modules 1042 that are configured to carry out the functions of embodiments of the invention.

A program/utility 1040, having the set (at least one) of program modules 1042, may be stored in the system memory 1028 by way of example, and not limitation, as well as an operating system, one or more application programs, other program modules, and program data. Each of the operating systems may have one or more application programs, other program modules, and program data or some combination thereof, and may include an implementation of a networking environment. The program modules 1042 generally carry out the functions and/or methodologies of embodiments of the invention as described herein.

The computer system 1012 may also communicate with a set of one or more external devices 1014 such as a keyboard, a pointing device, a display 1024, a tablet, a digital pen, etc. wherein these one or more devices enable a user to interact with the computer system 1012; and/or any devices (e.g., network card, modem, etc.) that enable the computer system 1012 to communicate with one or more other computing devices. Such communication can occur via Input/Output (I/O) interfaces 1022. These include wireless devices and other devices that may be connected to the computer system 1012, such as, a USB port, which may be used by a tablet device (not shown). Still yet, the computer system 1012 can communicate with one or more networks such as a local area network (LAN), a general wide area network (WAN), and/or a public network (e.g., the Internet) via a network adapter 1020. As depicted, a network adapter 1020 communicates with the other components of the computer system 1012 via the bus 1018. It should be understood that although not shown, other hardware and/or software components could be used in conjunction with the computer system 1012. Examples include, but are not limited to microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While particular embodiments have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at

What is claimed is:

1. A method that includes a processor and a local storage device accessible by the processor for storing information tailored to a user and a condition comprising:
   retrieving information from a set of online sources by a device;
   tailoring the retrieved information according to a criteria and the condition to form a curated data;
   storing the curated data on the local storage device;
   providing an index to access the curated data;
   receiving questions;
   utilizing the index to answer the received questions;
   responsive to identifying a question without an answer found in the curated data when the device is off-line, searching for the answer when the device is online; and
   responsive to finding the answer online,
      pruning the curated data by eliminating lower importance data as needed to store higher importance data based on an availability of space allocated to store the curated data on the local storage device, and
      updating the curated data stored on the local device.

2. The method of claim 1, wherein the criteria is a medical information prioritized by a medical needs of the user.

3. The method of claim 2, wherein the medical needs of the user is based on the condition.

4. The method of claim 3, wherein the condition is a chronic condition.

5. The method of claim 4, wherein the chronic condition is determined based on a user provided information and from a facility provided information.

6. The method of claim 3, wherein the condition is an acute condition.

7. The method of claim 6, wherein the acute condition is determined from a location and a time of year information.

8. The method of claim 7, further comprising:
   requesting the location and time of year information from a weather application; and
   receiving the location and time of year information from the weather application.

9. The method of claim 8, wherein the location and time of year information indicates a natural disaster.

10. An information handling system for storing information on a local storage device tailored to a user and a condition comprising:
   one or more processors;
   a memory coupled to at least one of the processors;
   a network interface that connects the local device to one or more remote web sites; and
   a set of computer program instructions stored in the memory and executed by at least one of the processors in order to perform actions comprising:
   retrieving information from a set of online sources by a device;
   tailoring the retrieved information according to a criteria and the condition to form a curated data;
   storing the curated data on the local storage device;
   providing an index to access the curated data;
   receiving questions;
   utilizing the index to answer the received questions;
   responsive to identifying a question without an answer found in the curated data when the device is off-line, searching for the answer when the device is online; and
   responsive to finding the answer online,
      pruning the curated data by eliminating lower importance data as needed to store higher importance data based on an availability of space allocated to store the curated data on the local storage device, and
      updating the curated data stored on the local device.

11. The information handling system of claim 10, wherein the criteria is a medical information prioritized by a medical needs of the user.

12. The information handling system of claim 11, wherein the medical needs of the user is based on the condition.

13. The information handling system of claim 12, wherein the condition is a chronic condition.

14. The information handling system of claim 13, wherein the chronic condition is determined based on a user provided information and from a facility provided information.

15. A computer program product for storing information on a local storage device tailored to a user and a condition stored in a computer readable storage medium, comprising computer program code that, when executed by an information handling system, performs actions comprising:
   retrieving information from a set of online sources by a device;
   tailoring the retrieved information according to a criteria and the condition to form a curated data;
   storing the curated data on the local storage device;
   providing an index to access the curated data;
   receiving questions;
   utilizing the index to answer the received questions;
   responsive to identifying a question without an answer found in the curated data when the device is off-line, searching for the answer when the device is online; and
   responsive to finding the answer online,
      pruning the curated data by eliminating lower importance data as needed to store higher importance data based on an availability of space allocated to store the curated data on the local storage device, and
      updating the curated data stored on the local device.

16. The computer program product of claim 15, wherein the criteria is a medical information prioritized by a medical needs of the user.

17. The computer program product of claim 16, wherein the medical needs of the user is based on the condition.

18. The computer program product of claim 17, wherein the condition is a chronic condition.

19. The computer program product of claim 18, wherein the chronic condition is determined based on a user provided information and from a facility provided information.

20. The computer program product of claim 19, wherein the condition is acute.

* * * * *